US008442771B2

(12) United States Patent
Wang

(10) Patent No.: US 8,442,771 B2
(45) Date of Patent: May 14, 2013

(54) METHODS AND APPARATUS FOR TERM NORMALIZATION

(75) Inventor: Xinglong Wang, Edinburgh (GB)

(73) Assignee: ITI Scotland Limited, Strathclyde (GB)

( * ) Notice: Subject to any disclaimer, the term of this patent is extended or adjusted under 35 U.S.C. 154(b) by 948 days.

(21) Appl. No.: 11/727,160

(22) Filed: Mar. 23, 2007

(65) Prior Publication Data

US 2008/0208837 A1 Aug. 28, 2008

(30) Foreign Application Priority Data

Feb. 27, 2007 (GB) .................................. 0703822.7

(51) Int. Cl.
*G01N 33/48* (2006.01)

(52) U.S. Cl.
USPC .......................................................... 702/19

(58) Field of Classification Search ..................... 702/19
See application file for complete search history.

(56) References Cited

U.S. PATENT DOCUMENTS

2006/0074991 A1* 4/2006 Lussier et al. ................ 707/200

OTHER PUBLICATIONS

Cohen et al., "A survey of current work in biomedical text mining", Briefings in Bioinformatics, 2005, vol. 6, No. 1, pp. 57-71.*

Roberts et al., "The automation of controlled vocabulary subject indexing of medical journal articles", Aslib Proceedings, 2000, vol. 52, No. 10, pp. 384-401.*

Ruch, "Automatic assignment fo biomedical categories: toward a generic approach", Bioinformatics, 2006, vol. 22, No. 6, pp. 658-664.*

Lee et al., "Exploring supervised and unsupervised methods to detect topics in biomedical text", BMC Bioinformatics, 2006, vol. 7, 11 pages.*

"Species" definition, online Merriam-Webster dictionary, 2012, on the world wide web at http://www.merriam-webster.com/dictionary/species, 2 pages.*

Chen et al; "Gene Name Ambiguity of Eukaryotic Nomenclatures"; Bioinformatics, vol. 21, Issue 2; 2005; pp. 248-256.

Tuason et al; "Biological Nomenclatures: A Source of Lexical Knowledge and Ambiguity"; Pacific Symposium in Biocomputing 9; 2004; pp. 238-249.

Robholz-Schuhmann et al; "Annotation and Disambiguation of Semantic Types in Biomedical Text: A Cascaded Approach to Named Entity Recognition"; Workshop on Multidimensional Markup with XML (XMLNLP), EACL 2006; pp. 11-18.

Krauthammer et al; Term Identification in the Biomedical Literature; Journal of Biomedical Informatics; vol. 37, Issue 6; 2004; pp. 512-526.

http://biocreative.sourceforge.net/biocreative_1_task1b.html, 2007, 2 pages.

Colosimo et al; Data Preparation and Interannotator Agreement: BioCreActivE Task 1B; BMC Bioinformatics 6 (suppl. 1): S11; 2005; pp. 1-8.

Hirschman et al; Overview of BioCreActivE Task 1B: Normalized Gene Lists; BMC Bioinformatics 6 (suppl. 1): S11; 2005; pp. 1-10.

* cited by examiner

*Primary Examiner* — Jerry Lin
(74) *Attorney, Agent, or Firm* — Nixon & Vanderhye PC

(57) ABSTRACT

Methods and data processing apparatus for normalization of mentions of subcellular entities, such as proteins and/or genes, in a natural language biomedical text document, in which the species of the individual mention of a subcellular entity is determined before an identifier is assigned to the individual mention of a subcellular entity and the identified species is taken into account when assigning an identifier to the said individual mention of a subcellular entity.

24 Claims, 4 Drawing Sheets

METHODS AND APPARATUS FOR TERM NORMALIZATION

This application is based on and incorporates herein by reference United Kingdom Patent Application No. GB 0703822.7 filed Feb. 27, 2007.

BACKGROUND OF THE INVENTION

The present invention relates to the natural language processing of biomedical text. In particular, the invention relates to methods and data-processing apparatus for carrying out term normalization of individual mentions of subcellular entities in natural language biomedical texts which address the problem of disambiguating between subcellular entities from organisms of different species that may be represented in natural language biomedical text using identical character strings.

Within this description and the appended Claims, "term normalization" refers to a natural language processing procedure in which a mention of an entity is assigned a normalized identifier which uniquely denotes the entity to which that mention refers. Thus, different character strings which may be used to refer to the same entity in natural language text can be represented by the same identifier in subsequent processing. Typically, the identifier will be an identifier of data concerning that entity in a database. The database will typically include a character string which represents a canonical name for the entity.

The present invention relates in particular to the term normalization of mentions of subcellular entities in natural language biomedical text documents, such as scientific papers, including conference proceedings, and patent publications.

Within this description and the appended claim, the term "subcellular entities" includes genes and other DNA sequences (such as non-coding DNA), proteins (irrespective of length), other macromolecules (for example, fatty acids, polysaccharides, and RNA such as mRNA, tRNA, rRNA, dsRNA and non-coding RNA), and also intra-cellular structures, such as organelles, whether or not they are located within a cell in the context of the document which is being analysed and whether or not they originate from a cell. For example, the term includes viral proteins, genes, macromolecules and structures.

It has been found that mentions of subcellular entities in natural language biomedical text are frequently ambiguous. Ambiguity arises from several sources. Biologically-relevant entities may have multiple names which are in common use, such as acronyms, abbreviations, synonyms and morphological variations; a single name can refer to more than one biological entity; and common English words are often used to refer to subcellular entities. The problem of ambiguity is especially severe when the text which is to be analysed may relate to one or more of a number of species of model organisms. In practice, the biomedical literature discusses subcellular entities from a great many species.

By way of example, table 1 shows three abbreviated records taken from the RefSeq protein database (see the ncbi website with the extension "nlm.nih.gov/RefSeq"). The protein known as interleukin 5 precursor (i.e., NP__00870) may well occur in natural language biomedical text as one of its synonyms such as interleukin 5 or IL5, and sometimes even Interleukin-5 or IL-5, which are not recorded here. Furthermore, the term IL5 may denote any of three proteins shown below, which present a problem for a natural language term identification system.

TABLE 1

| RefSeq ID | Species | Protein Synonyms |
|---|---|---|
| NP__000870 | *Homo Sapiens* | interleukin 5 precursor; interleukin 5; IL5 |
| NP__068606 | *Rattus Norvegicus* | interleukin 5; IL5 |
| NP__783851 | *Homo Sapiens* | interleukin 5 receptor, alpha isoform 2 precursor; IL5 |

To date, the problem of ambiguity between species has been considered to present a serious problem for natural language processing. Research work has been carried out to study the ambiguity in biological names. For example, Chen et al. investigated gene name ambiguity and quantified the extent to which the use of the same gene names across various model organisms leads to gene name ambiguity in general (Chen, L., Liu, H., and Freidman, C., Bioinformatics, Vol. 21, No. 2, 2005, pp 248-256). Chen et al. encouraged authors of biomedical publications and journal editors to use only official symbols and to avoid using aliases, particularly those that coincide with other English language words, and to revise naming conventions to reduce ambiguity. Chen et al. proposed the development of techniques to categorise an article based on domain or species, to help reduce ambiguity. However, even if an effective method of categorising articles based on domain or species was developed, this would not, in itself, facilitate the accurate normalization of terms in a document relating to organisms from more than one species.

The normalization of gene names across data sets relating to several different species was addressed by BioCreAtIve I, Task 1B, Gene Normalization (see the biocreative.sourceforge website with the extension ".net/biocreative__1_task1b.html"). However, in this task, each analysed abstract related only to a single species, which was known. It is a separate problem to accurately normalize terms in a document which may relate to organisms from more than one species.

Accordingly, the present invention seeks to address the problem of carrying out term normalization of mentions of subcellular entities in biomedical natural language text documents while disambiguating, where possible, between species. Of course, one skilled in the art will appreciate that term identification is not a perfect science and it will not always be possible to correctly identify the species of a mentioned subcellular entity.

SUMMARY OF THE INVENTION

The exemplary method and apparatus of the present invention provide term normalization in which the species of individual mentions of subcellular entities in a biomedical text document are identified from the context of the individual mentions of subcellular entities prior to the assignment of identifiers to the individual mentions of subcellular entities, taking into account the identified species of the individual mentions of subcellular entities.

The performance of exemplary methods and apparatus according to the present invention has been measured and found to exceed 85% of inter-annotator agreement. The invention facilitates the identification of the species of individual mentions of subcellular entities in biomedical text documents which may include mentions of subcellular entities from more than one species and is of particular benefit where the biomedical text document may include mention of subcellular entities from more than one species which might be denoted by identical character strings in natural language biomedical text.

An exemplary embodiment and exemplary method creates a group of one or more candidate identifiers by searching a lexicon using character strings which match the individual mention of a subcellular entity, using an exact or approximate matching algorithm, and then producing a revised group comprising the identifiers for which the species of the subcellular entity referred to by the identifiers is the identified species of the individual mention of the subcellular entity. If the identifier remains ambiguous, a heuristic rule is used to select an identifier to be assigned to an individual protein mention.

In an example embodiment, the species of individual mentions of subcellular entities is identified from the context of individual mentions of subcellular entities using a machine trained algorithm which take into account the text in a window around the individual mentions of subcellular entities. In an alternative example embodiment, the step of identifying the species of the individual mention of the subcellular entity from the context of the individual mention of the subcellular entity determines the species of the individual mention of the subcellular entity by looking for species words which are close to the individual mention of a subcellular entity in the biomedical text document.

DESCRIPTION OF THE DRAWINGS

An example embodiment of the present invention will now be illustrated with reference to the following Figures in which.

DETAILED DESCRIPTION OF AN EXAMPLE EMBODIMENT

Within this specification and the appended claims, the term "biomedical literature" includes scientific papers and patent publications which relate to biological, biotechnological or medical subject matter and the term also includes abstracts of larger documents.

Within this specification and the appended claims, the term "character string" includes sequences of letters, numbers and/or other punctuation symbols generally used in biomedical literature to denote subcellular entities, and may optionally include letters, numbers and/or other punctuation symbols in more than one style, for example characters in superscript or subscript. The character strings typically comprise characters according to a recognised international character repertoire such as ASCII, ISO-646, or ISO/IEC 10646 (Unicode).

Within this specification and the appended claims, the term "lexicon" includes data comprising, in respect of a plurality of entities which are identified by identifiers, at least one or more character strings which may be used to represent the entities. A lexicon may comprise more than one database. The lexicons used in the present invention also include data concerning the species of the entities, or data which can be used to establish the species of the entities. A lexicon may be an ontology. A lexicon may be part of an ontology. A lexicon may be extracted from an ontology.

Within this specification and the appended claims, the term "species" refers to any taxonomic group of organisms which can interbreed.

The following example embodiment discusses the identification of the species of proteins in biomedical literature. However, the same procedure can be applied to the term normalization of other subcellular entities.

Figure 1:
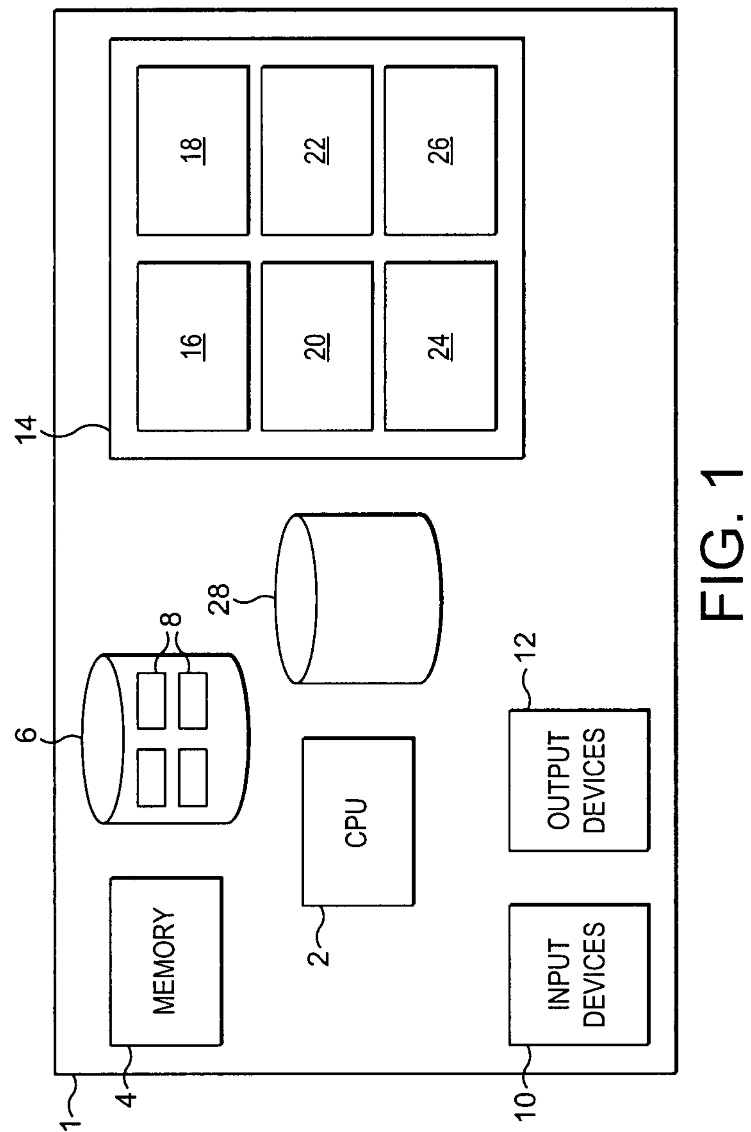
FIG. 1 is a schematic diagram of data-processing apparatus for carrying out natural language processing.

FIG. 1 is a schematic diagram of example data-processing apparatus 1 for carrying out a generic natural language processing procedure. The data-processing apparatus comprises a CPU 2, memory 4 and a storage device 6, such as a hard disc drive, which stores a plurality of biomedical text documents 8 in the form of XML documents derived from original biomedical documents by procedures such as scanning and optical character recognition of printed documents, and/or the automatic pre-processing of documents received in format such as XML, HTML or portable document format (pdf). The biomedical text documents are typically English language. However, the apparatus can be readily adapted to process biomedical text documents in other languages such as French, German, Japanese, Chinese or Russian. The data-processing apparatus further comprises one or more input devices 10, such as a keyboard and/or internet protocol interface, and one or more output devices 12 such as a display screen or internet protocol interface.

The apparatus further comprises a natural language processing module 14 in the form of computer program code, which is executed on the CPU in use, and which further comprises a plurality of natural language processing modules such as a tokenisation module 16, a part of speech tagging module 18, a lemmatisation module 20, a chunking module 22, a named entity recognition module 24, and a term normalization module 26. The data-processing apparatus may be implemented as a standalone computer or using a network of computers and storage devices, such as a LAN or WAN.

The apparatus further comprises a lexicon 28, in the form of one or more databases which includes data concerning a plurality of different proteins, some of which are referred to using identical character strings in natural language biomedical text, which presents a problem for term normalization software. The lexicon may comprise an entry for each protein, which is referenceable by a unique identifier, such as an accession number, reference number or other code which identifies that protein according to a scheme. For example, the identifier may be the RefSeq ID number of a protein (see the ncbi website at with the extension "nlm.nih.gov/RefSeq/"), or its accession number in another database, such as Cognia Molecular (Cognia Molecular is a trade mark of Cognia Corporation Inc., New York). However, the identifier may have any appropriate form and could, for example, simply be a character string which is a canonical form of the protein.

Typically, the entry in the lexicon for each protein includes data concerning synonymous character strings which are used in natural language biomedical text to denote the protein, as well as a character string which denotes a canonical form of that entity. An exemplary lexicon comprises a plurality of entries for different proteins, each of which comprises an entity identifier, the species of the model organism of the protein, a canonical name for the entity (as a character string) and synonyms for the entity (as character strings). At least some of the synonyms within the lexicon are identical for different proteins, presenting a term normalization problem as simple text matching is not sufficient to disambiguate between such proteins. However, the term normalization procedure may be implemented using a lexicon in a different format, such as a database comprising a list of character strings which are known synonyms of more or more proteins and, for each synonym, identifiers of the proteins which are referred to using that character string in natural language biomedical text, provided that the species of the proteins can be determined from data in the lexicon (e.g. because the lexicon comprises the species of the protein, or because the lexicon comprises data which can be used to look up the species of the protein in another data source). The lexicon may be implemented using one or more databases in any suitable database format, such as hierarchical, relational or object databases.

Figure 2:
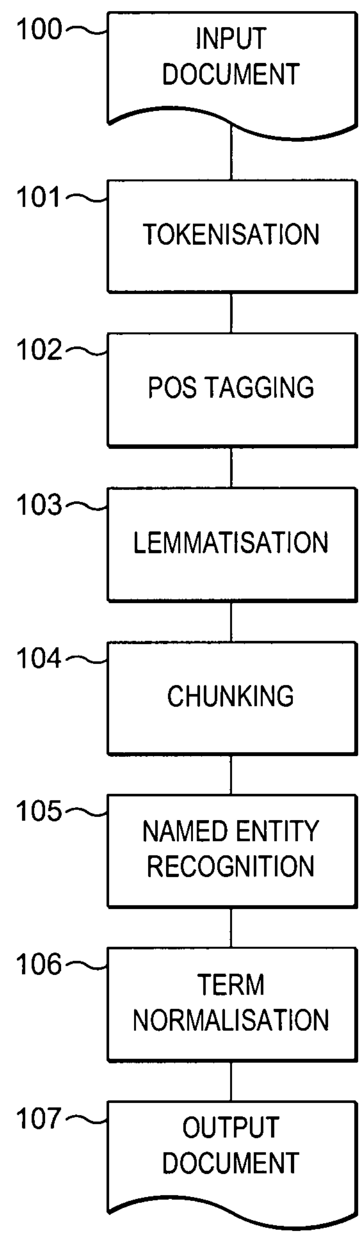
FIG. 2 is a flowchart of a generic natural language processor procedure.

FIG. 2 illustrates a generic natural language processing pipeline implemented by the apparatus of FIG. 1. An input biomedical text document 100 is the subject of successive tokenisation 101, part of speech tagging 102, lemmatisation 103, chunking 104, named entity recognition 105 and term normalization 106 steps, carried out by the corresponding natural language processing module. The resulting output document 107 includes annotations including information derived from the successive natural language processing steps and includes, where possible, a single normalized identifier of at least one type of entity, such as genes or proteins, which were identified by the named entity recognition module. The innovation in the present invention relates to the term normalization step, and the other stages of the natural language processing pipeline may be implemented using known modules, well known to those skilled in the art.

Figure 3:
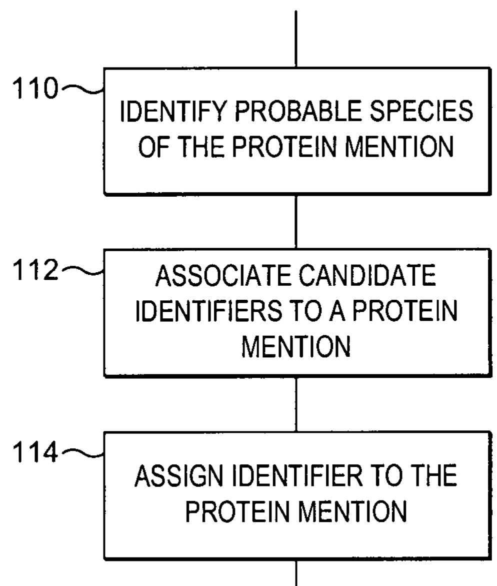
FIG. 3 is a flowchart of a term normalization procedure according to the present invention.

With reference to FIG. 3, an exemplary term normalization procedure according to the invention comprises the step, for each individual mention of a protein in a document, of determining the probable species of the protein mention from the context of the protein mention 110. Each protein mention is then associated with one or more candidate identifiers 112 using a candidate identifier selection module. A single most probable identifier is then assigned to the protein mention 114, by a procedure which selects an identifier from the group of previously identified candidate identifiers and the identified probable species of the individual protein mention.

The steps of identifying the probable species of the protein mention and associating candidate identifiers to a protein mention may take place in either order, simultaneously or iteratively. In some implementations, the step of associating candidate identifiers with a protein mention may take into account the identified species of the protein mention. However, a probable species of the protein mention will be determined from the context of the individual protein mention before a single identifier is finally assigned to the protein mention, except that this stage may be omitted on occasions when a single identifier can be assigned by other methods, for example where it can be established from an exact or approximate matching step that the protein mention matches only one candidate identifier in the lexicon. We have found that this enables disambiguation by species in many circumstances in natural language biomedical text documents, as evidenced by the experimental data provided below.

We propose to treat the assignment of a species to a protein mention as a text classification problem and have developed two alternative species identification modules which assign a species to individual protein mentions to determine whether the piece of context surrounding a protein mention centres on a particular species of interest, where the context is represented by a set of features.

The first species identification module is rule-based. A list of species terms, which indicate specific species, is compiled. For example, mouse is a species term indicating *mus musculus*, and *Escherichia coli* is a species term for *Escherichia coli*. If one of these species terms appears near a protein name, this protein mention can be assumed to belong to the species that the species term indicates. The species term which is closest to the protein mention (measured in terms of the number of tokens between the species term and the protein mention) is selected. When two species terms appear an equal distance to the left hand side and the right hand side of a protein mention, we assign the protein mention the species indicated by the species term on the left. When two species terms appear an equal distance away from the protein mention, and when the text is in a language other than English, it may be more appropriate to select the species term which follows the protein mention, or the species term which precedes the protein mention depending on the language and/or the script of the text document. The preferred alternative can be established empirically for a particular language. By "follows the protein mention" we mean after the protein mention in the direction in which the script is written, which may be left-to-right, right-to-left, top-to-bottom or a combination of these directions. "Precedes the protein mention" refers to the opposite direction.

The second species identification module uses a machine learning algorithm. The training data for the algorithm was derived from the manually annotated data. As long as a protein mention is normalized with protein identifiers, the species can be found by looking up the lexicon. The machine learning algorithm used a WEKA (Waikato Environment for Knowledge Analysis) implementation of Support Vector Machines (SVM) algorithm (obtainable from the University of Waikato, Waikato, New Zealand, see the cs.waikato website with the extension "ac.nz/~ml/weka/"). This algorithm maps the set of training data into a higher dimensional feature space F via a mapping function Ø and then constructs a separating hyperplane with maximum margin. The features used are contextual word lemmas within a window size of 50, where the lemmas are weighted using a term frequency-inverse document frequency weight. The resulting trained algorithm can be used to assign a species to an individual protein mention.

Lexicon Expansion

Figure 4:
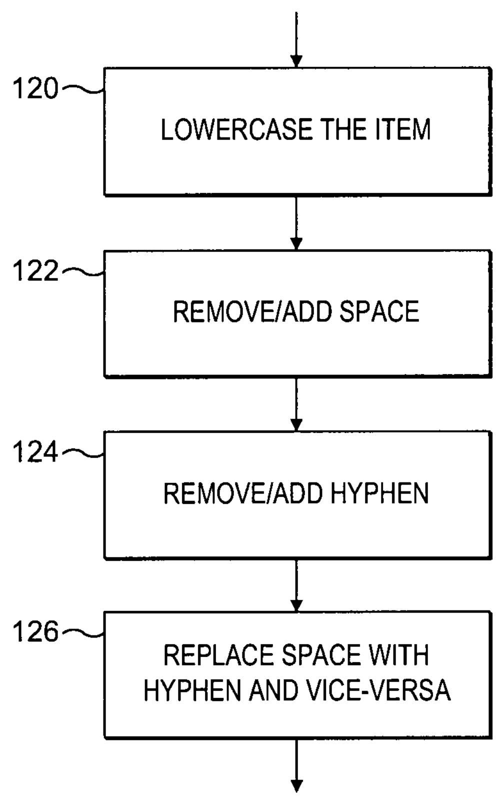
FIG. 4 is a flowchart of procedures used to expand a lexicon.
Figure 5:
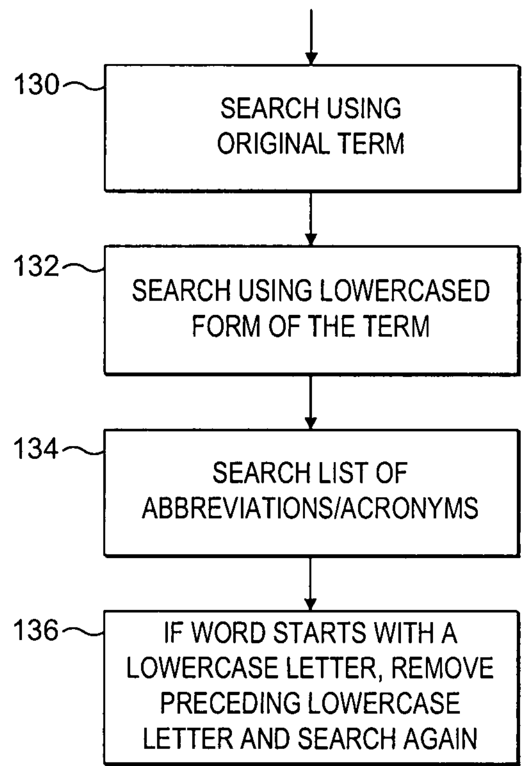
FIG. 5 is a flowchart of search steps in a procedure to associate candidate identifiers to a protein mention.

The step of assigning candidate identifiers to a protein mention makes reference to the lexicon, and the character strings stored in the lexicon. The lexicon can be expanded before the procedure is carried out by implementing the rules illustrated in the flowchart of FIG. 4.

Firstly, each entry is converted to lower case 120, and a new entry is added to the lexicon if the lower case version is not already included. For each entry, spaces are removed or added 122 as appropriate between w and x, (e.g. "TEG 27"⇒"TEG27"), where w denotes a token with multiple letters, and $x \in D \cup L \cup G$, where D are tokens containing digits only, L are tokens containing a single letter only and G denotes the set of English spelling equivalents to Greek letters (e.g. alpha, beta, etc.). The lexicon is also enriched with terms formed by removing or adding a hyphen between w and x 124 (e.g. "TEG-27"⇒"TEG27"). In addition, the lexicon is enriched with entries in which a space between w and x was replaced with a hyphen and vice versa 126 (e.g. "TEG 27"⇒"TEG-27"). This procedure expanded the number of different synonyms in a test lexicon from 153,997 to 186,683.

Associating Candidate Identifiers to a Protein Mention

The step of associating candidate identifiers to a protein mention comprises the steps of carrying out the following procedures, preferably in the sequence shown, using each individual protein mention. Each procedure generates a variant of the mention and then compares it to all entries in the lexicon, thereby functioning as an approximate matching algorithm. The identifiers of matching proteins are then retrieved and included in a group of candidate identifiers. The procedures are as follows:

1. The lexicon is searched using the original term (i.e. the character string denoting the individual protein mention) found in the document which is being analysed 130;
2. The lexicon is searched using a character string in which upper case letters in the original term are replaced with their lower-case equivalents;
3. The document is searched using an algorithm for identifying abbreviations (Schwartz, A., and Hearst, M., A simple algorithm for identifying abbreviations in biomedical texts, in Proceedings of the Pacific Symposium on Biocomputing, 2003). If a list of abbreviations/acronyms or long form pairs is present in the document which is being analysed, then, if the protein mention is in the list, its partner is searched for in the lexicon 134;
4. If a protein mention starts with a lower-case letter, followed by an upper-case letter, the preceding lower-case letter is removed, and the resulting character string is searched for in the lexicon 136. For example, if the protein mention is "hDAK1", the lexicon would be searched for "DAK1". The rationale behind this fourth rule is that the preceding lower-case letter may be deliberately added by the authors of a biomedical text document to denote the species of a protein mention, whereas the lexicon may only contain an unmodified form of the protein, without the prefix which indicates species.

If only one character string is identified by this procedure, then the group of candidate identifiers associated with that character string is retrieved from the lexicon. (The group of candidate identifiers may comprise a single identifier.) If more than one character string is identified, for example, where more than one synonym is retrieved after searching the lexicon, the group of candidate identifiers comprising the union of the groups of candidate identifiers associated with each identified character string, is retrieved.

Figure 6:
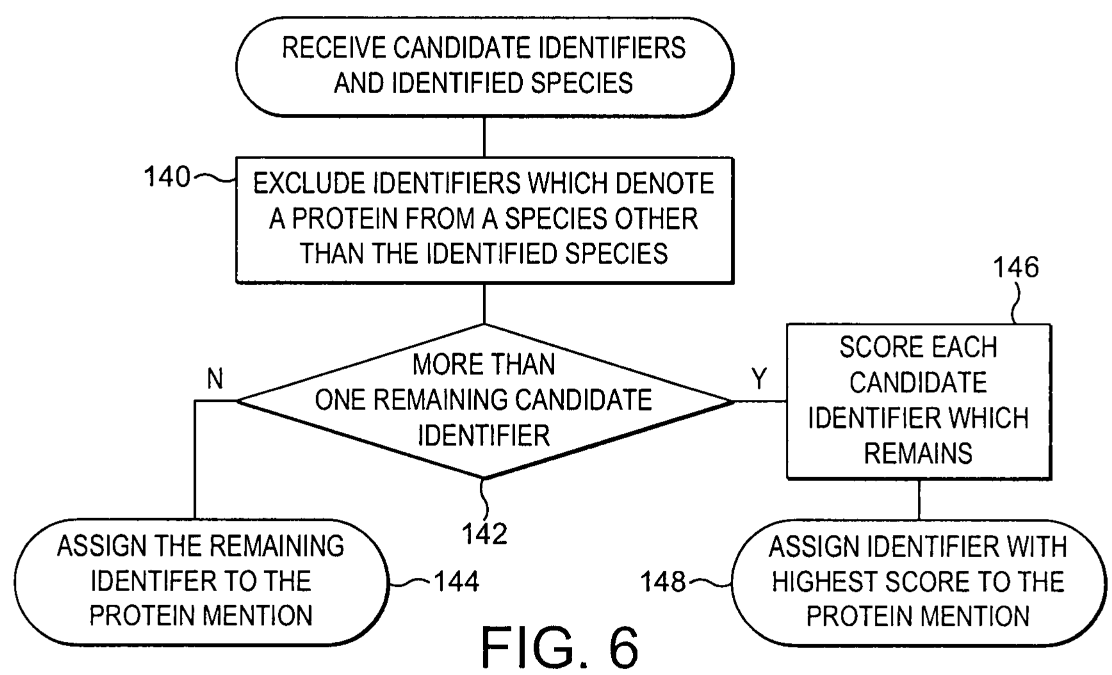
FIG. 6 is a flowchart of a heuristic procedure for selecting a single protein identifier from a group of candidate protein identifiers.

If only one candidate identifier has been identified, then this identifier could be assigned to the protein mention in question. However, the procedure will frequently lead to a group of more than one identifier being retrieved from the lexicon. In this case, the group of candidate identifiers is revised by excluding candidate identifiers which denote a protein from a species other than that which has been assigned by the species identification module. With reference to FIG. 6, the group of candidate identifiers associated with an individual protein mention is revised 140 by excluding any identifier which denotes a protein from a species other than the species which has been assigned by the species identification module. The group of candidate identifiers can be revised by removing candidates from the group or by creating a new group. The group of candidate identifiers may be revised in this way after one or more individual steps of the approximate matching algorithm, after an exact matching step and before carrying out an approximate match, and/or after the completion of the approximate matching steps.

If this leaves only one candidate identifier 142, then that identifier is assigned to the protein mention 144. Otherwise, a heuristic rule is used which selects an identifier from the group of one or more candidate identifiers on the basis of data which is known to be correlated to the likelihood that the identifier is the correct identifier of a protein mention. In this case, we have found that a heuristic rule which favours proteins with lower numbered identifiers improves the accuracy of term normalization when using Cognia Molecular and, we would expect, RefSeq ID numbers.

If a protein mention (m) is still ambiguous and has multiple candidate identifiers, we use the algorithm described below to calculate a score 146 for each occurrence of these identifiers and scores for the same identifiers are accumulated. The identifier bearing the highest accumulated score 148 is assigned to a protein mention.

Where n synonyms of a protein mention m have been retrieved from the lexicon, the set of synonyms is denoted as $S=\{s_1, s_2, \ldots, s_i, \ldots s_n\}$, where each synonym $s_i$ maps to a set of protein identifiers: $ID_{si}=\{id_{si}, id_{si2}, \ldots, id_{sij}, \ldots id_{sim}\}$. m is the number of identifiers that a synonym $s_i$ has. Therefore, $ID=\cup_{i=1}^{i=n} ID_{s_i}$ where $ID_{si}$ is the set of candidate identifiers that need to be considered. Note that an identifier $id_i$ in ID may occur in multiple sets. For example, $id_i$ may occur in both $ID_{s1}$ and $ID_{s2}$. An occurrence of $id_i$ is scored in a way that, if it is the lowest numbered identifier in $ID_{si}$, it is assigned a score of 3; otherwise it is assigned a score of 1. This weighting rewards the lowest numbered identifier in an arbitrary set $ID_{si}$. Scores for all occurrences of $id_i$ are then accumulated. This procedure is repeated for every $id_i$ in ID, where $i \in [1,|ID|]$, and the identifier $id_i$ that bears the highest accumulated score is assigned to the protein mention m, for example, by annotating the biomedical text document.

EXAMPLE

In an example of the application of the term normalization procedure, a protein mention comprises the character string IL-5. The example lexicon includes the character strings listed below as synonyms of relevant proteins.

| Character String | Identifiers Denoted by Character String |
|---|---|
| IL-5 | P00495103 P00665873 |
| IL5 | P00495103 P00665873 P00705339 |
| Interleukin 5 | P00665873 |

The protein identifiers P00495103 and P00665873 would be found by exact matching and the protein identifier P00705339 would be found following an approximate match which searched the lexicon for the character strings IL5 and Interleukin 5. The resulting group of candidate identifiers ID comprises P00495103, P00665873 and P00705339.

If it is known from data included in the lexicon, or which can be obtained from another data source using data included in the lexicon, that P00495103 relates to the species *homo sapiens* and P00665873 and P00705339 relate to the species *mus musculus* then, if the species of the individual mention of IL-5 has been identified as *homo sapiens*, the identifier P00495103 can be assigned to the mention of IL-5 without use of the heuristic rule. If, however, the species of the mention of IL-5 is identified as *mus musculus*, a revised group comprising only P00665873 and P00705339 is prepared and the heuristic rule described above is used to determine which identifier should be assigned to the protein mention. By the given formula, P00665873 has a score of 5 and P00705339 has a score of 1 and so P00665873 is assigned to the protein mention.

It is surprising that this strategy is beneficial; this may arise from there being an underlying structure in the Cognia Molecular database. For example, identifiers may be allocated to new proteins consecutively, so that larger numbers of proteins were more recently identified, and may therefore be found less often in texts. Alternatively, identifiers may be assigned scores by another method, such as taking into account the date on which the protein was assigned as a record in the database, or another score, such as a score indicating frequency with which that protein is found in natural language text, may be used.

This rule can be modified by more sophisticated methods of scoring identifiers. It may be found that, with some data sources, the highest numbered identifier should be assigned a high weighting. In general, the identifier may be selected from the group of one or more candidate identifiers on the basis of data which is known to be correlated to the likelihood that the identifier is the correct identifier of a protein mention. This may be by a process which will always produce the same outcome, or produce one of a range of outcomes with the same probability distribution, independently of the species or context of the individual protein mention.

Other variations and modifications will be apparent to one skilled in the art. As well as for the identification of proteins, the procedure can be applied to the normalisation of other subcellular entities which are mentioned in biomedical text, such as genes, macromolecules and subcellular structures. Although the example embodiments relate to the analysis of English language text, one skilled in the art will appreciate that the methods of the present invention may be applied to the analysis of other languages such as French, German, Chinese, Russian or Japanese, by appropriate customisation. The invention may be used to analyse biomedical texts which include a mixture of languages and/or scripts. The invention may be used to analyse biomedical text documents which include a script which reads from left to right, right to left, top to bottom, or a mixture of directions.

Although the embodiments of the invention described with reference to the drawings comprise methods performed by data-processing apparatus, and also data-processing apparatus, the invention also extends to computer program instructions, particularly computer program instructions on or in a carrier, adapted for carrying out the processes of the invention or for causing a computer to perform as the data-processing apparatus of the invention. Programs may be in the form of source code, object code, a code intermediate source, such as in a partially compiled form, or in any other form suitable for use in the implementation of the processes according to the invention. The carrier may be any entity or device capable of carrying the program instructions.

For example, the carrier may comprise a storage medium, such as a ROM, for example a CD ROM or a semiconductor ROM, or a magnetic recording medium, for example a floppy disc or hard disc. Furthermore, the carrier may be a transmissible carrier such as an electrical or optical signal which may be conveyed via electrical or optical cable or by radio or other means. When a program is embodied in a signal which may be conveyed directly by cable, the carrier may be constituted by such cable or other device or means.

Experimental Results

Experiments were carried out using the Cognia Molecular database as a reference protein database for manual annotations of biomedical text and also to provide lexicon data for use with the term normalization software. The Cognia Molecular database was derived from an early version of RefSeq and, similarly to RefSeq, it comprises entries concerning proteins from many species.

Manual annotations were made in respect of 584 documents, which were abstracts or full-paper articles taken from PubMed Central. (PubMed is a trademark of the National Library of Medicine). Every protein mention in a document was assigned the single, unique identifier of that protein in the Cognia Molecular database. The annotators were specifically asked to pay attention to the species of protein mentions.

For instance, if a protein mention occurred more than once in different pieces of context, referring to different species, the annotators would normalize them to different Cognia Molecular identifiers referring to the protein from organisms from the appropriate species.

Annotated documents were split into three folds: 64% of the annotated documents were used as training data, 16% were used as development test data, and 20% were used as blind test data. (The term "training data" is used to refer to data for use in training a machine learning system, the term "development test data" is used to refer to data for use in tuning the parameters of a machine learning system which has been trained using training data, and the term "blind test data" is used to refer to data which has not been previously analysed by the machine learning system and can therefore be used to obtain an unbiased measure of the performance of the machine learning system.)

Analysed training data was categorised as follows (percentages refer to the proportion of annotated protein mentions in the 584 manually annotated training data documents).

(1) Correctly normalized (24.3%): a unique identifier was found in the lexicon and assigned to a protein term;

(2) Unknown (1.63%): annotators could not determine the identification of the protein, and therefore were not able to assign identifiers to them;

(3) Not available in the lexicon (2.48%): annotators could identify the protein and its species but could not find a corresponding identifier in the lexicon;

(4) Species overriding (68.5%): the annotators recognised a protein name and found proteins with that name in the lexicon; however, there was not an identifier specific to that protein from the correct species. In these cases, annotators were advised to assign correct species in their opinion to the protein mentions. They could also use keyword 'general' to refer a general use of a protein and keyword 'unknown' to denote unknown cases;

(5) Experimental proteins but not real proteins (3%);

(6) Protein complex (0.05%).

For subsequent experiments, we only made use of the portion of the data that was correctly normalized (i.e., category (1)), because only protein mentions in this portion were assigned with a unique identifier from the lexicon.

Measuring Inter-Annotator Agreement and Term Normalization Performance

A portion of the data (5%) was double-annotated, and used to calculated inter-annotator agreement (IAA), using only the intersection of terms which were properly normalized by both annotators (i.e. data which falls into category (1) above). In detail, we arbitrarily took one annotation as gold standard, and the second as system output, and calculated an F1 score (using Equation 3 below) on the second annotation. The inter-annotator agreement (IAA) on term normalization is 69.55%, which we think is reasonable, given that IAA was only about 67.0% for gold-standard data for the Word Sense Disambiguation task discussed in Mihalcea, R., Chklovski, T. and Killganiff, A., "The Senseval-3 English lexical sample task", in the Proceedings of the Third International Workshop on the Evaluation of Systems of the Semantic Analysis of Text (Senseval-3), 2004. In the Word Sense Disambiguation task, native speaking annotators were asked to disambiguate uses of common English words such as "bank", instead of protein mentions.)

The precision, recall and F1 measurements of the performance of the term normalizer were carried out using the following equations:

$$\text{precision} = \frac{\text{\# of Correctly Normalized By Term Normalizer}}{\text{\# of Total Normalized By Term Normalizer}} \quad \text{(Equation 1)}$$

$$\text{recall} = \frac{\text{\# of Correctly Normalized By Term Normalizer}}{\text{\# of Total Normalized In Gold Standard}} \quad \text{(Equation 2)}$$

$$F1 = \frac{2 \times \text{precision} \times \text{recall}}{\text{precision} + \text{recall}} \quad \text{(Equation 3)}$$

Comparison of Term Normalization Procedures

Four term normalization procedures were compared in the first instance. In each case, candidate identifiers associated with individual protein mentions were identified by the procedure discussed above. In the first term normalization system, an arbitrary identifier from the list of candidate identifiers was then selected as the normalized form of the protein mention. In a second system, the protein mention was assigned the identifier, in the pool of candidate identifiers, which has the lowest value.

In a third system, we used a Vector Space Model (VSM). In detail, to disambiguate a protein mention (m), from n candidate identifiers, we represented the context that m appears in as a vector of N word features, which we call a 'context' vector, where each feature has an 1 or 0 value to indicate occurrence or absence of a non-functional context word. Similarly, we built n 'definition' vectors for all of the candidate identifiers, where 'definition' means description (i.e., synonyms, species, etc) of an identifier using data found in the lexicon. The 'context' vector' was then compared with the 'definition' vectors. The identifier with a 'definition' vector that is most similar to the 'context' vector, as measured by cosine score, is assigned to the protein mention. Equation 4 measures cosine similarity, where $\vec{v}$ and $\vec{w}$ are vectors and N is the dimension of the vector space.

$$\text{corr}(\vec{v}, \vec{w}) = \frac{\sum_{i=1}^{N} \vec{v}_i \vec{w}_i}{\sqrt{\sum_{i=1}^{N} \vec{v}_i^2 \sum_{i=1}^{N} \vec{w}_i^2}} \quad \text{(Equation 4)}$$

The fourth system was the exemplary embodiment discussed above with reference to FIGS. 1 to 6.

The performance of the four systems was compared and the results are shown in Table 2. The fourth system which identified the likely species of a protein mention from context prior to assigning an identifier to a protein mention performed the best by a large margin. Surprisingly, system 2 significantly outperformed system 1, which indicated that the ordering of identifiers in the lexicon is not arbitrary: if an ambiguous protein mention corresponds to a set of candidate identifiers, the lowest number is more likely to be the correct identifier. This is one of our motivations for the heuristic rule described above with reference to FIG. 6.

TABLE 2

Performance (%) of the Four Term Normalization Systems Evaluated Using the Development Test Data

| System | Precision | Recall | F1 |
|---|---|---|---|
| 1 | 47.3 | 41.1 | 44.1 |
| 2 | 52.1 | 46.4 | 49.1 |
| 3 | 48.9 | 43.5 | 46.0 |
| 4 | 4.1 | 55.5 | 59.5 |

System 3 did not perform as well as we expected. One of the reasons might be that the glosses of identifiers in the lexicon which we used might be too short, which causes the 'definition' vectors to be too sparse to produce convincing results. Better results might be obtained using a lexicon that has more extensive descriptions for its protein entries. Smoothing techniques might also alleviate the data sparseness problem.

Table 3 shows 10-fold cross-validation performance on species-tagging, using machine and rule-based learning respectively. It shows that the machine learning approach outperformed rule-based approach by 6.6% on average. It may be possible to train the machine learning algorithm using training date which is obtained training data automatically, using rules and the list of monosemous words that are strong indication of species.

TABLE 3

| | Experiments | | | | | | | | | | |
|---|---|---|---|---|---|---|---|---|---|---|---|
| | 1 | 2 | 3 | 4 | 5 | 6 | 7 | 8 | 9 | 10 | avg |
| ML-ST | 41.0 | 69.5 | 6.4 | 53.9 | 47.8 | 36.8 | 48.6 | 68.8 | 71.9 | 55.0 | 56.0 |
| R-ST | 50.2 | 40.6 | 64.2 | 67.4 | 52.1 | 22.0 | 44.8 | 49.3 | 35.6 | 67.5 | 49.4 |

Finally, the best term normalization results were achieved by the procedure described above and illustrated with reference to FIGS. 1 through 6. Table 4 shows the precision, recall and F1 of the example term normalizer, as evaluated on the development test data, together with the value of IAA, which is an indicator of the performance by human annotators in the same task. The term normalization system achieved a performance which exceeded 85% of IAA which we believe to be promising.

TABLE 4

| Dataset | IAA | ST Accuracy | Precision | Recall | F1 |
|---|---|---|---|---|---|
| Development test data | 69.55 | 75.6 | 64.14 | 55.5 | 59.51 |

Further variations and modifications may be made within the scope of the invention herein disclosed.

What is claimed is:

1. A method of using a data-processing apparatus, having a processor, to normalize an individual mention of a subcellular entity within a biomedical text document, the method comprising using the data-processing apparatus to carry out:

inputting said individual mention of a subcellular entity;

selecting a group of identifiers of subcellular entities, said subcellular entities being referred to in biomedical text with the same character string and being from different species, each of said species being a taxonomic group of organisms which can interbreed;

generating, using said processor, a species identifier that identifies the species of said individual mention of a subcellular entity from the context of said mention of a subcellular entity;

selecting an identifier from said group of identifiers, taking into account the species identifier that identifies the species of said individual mention of a subcellular entity; and outputting said identifier to provide a normalized reference to said subcellular entity.

2. A method according to claim 1, wherein the method comprises the step of creating a group of one or more candidate identifiers by searching a lexicon comprising character strings which are used in biomedical text documents to refer to subcellular entities for character strings which match the individual mention of a subcellular entity, either as exact matches or using an approximate matching algorithm, and including the identifiers of the matched subcellular entities in the group of one or more candidate identifiers.

3. A method according to claim 2, wherein the lexicon comprises data concerning the species of subcellular entities having a particular identifier, and wherein, when the said group of one or more candidate identifiers comprises a plurality of candidate identifiers, the method further comprises the step of revising the group to produce a group comprising only identifiers, selected from the said group of one or more candidate identifiers, for which the species of the subcellular entity referred to by the identifiers is the identified species of the mention of the subcellular entity, thereby taking into account the identified species of the said individual mention of a subcellular entity.

4. A method according to claim 2, wherein an identifier is selected from the group of one or more candidate identifiers, or a revised group of candidate identifiers selected from the said group of one or more candidate identifiers, using a predetermined algorithm or heuristic.

5. A method according to claim 4, wherein the identifier is selected from the group of one or more candidate identifiers on the basis of data which is known to be correlated to the likelihood that the identifier is the correct identifier of a protein mention.

6. A method according to claim 4, wherein the predetermined algorithm or heuristic selects an identifier from the group of one or more candidate identifiers on the basis of the values of the identifiers.

7. A method according to claim 1, wherein generating said species identifier comprises using a machine trained algorithm which takes into account the text in a window around the said individual mention of a subcellular entity in the biomedical text document.

8. A method according to claim 1, wherein generating said species identifier comprises determining the species of the said individual mention of the subcellular entity by looking for species words which are close to the individual mention of a subcellular entity in the biomedical text document.

9. A method according to claim 1, wherein the biomedical text document includes mentions of subcellular entities relating to more than one species of organism.

10. A method according to claim 9, wherein at least one pair of the said mentions of subcellular entities is denoted by an identical characters string but relate to different species and the method will, in at least some cases, assign different identifiers to the said mentions of subcellular entities dependent on the species of the individual mentions of subcellular entities responsive to species determining contextual information around the said individual mentions of the species in the biomedical text document.

11. A method according to claim 1, wherein the subcellular biological entity is a protein.

12. A storage medium having a set of instructions executable by a computer, for causing the processor to carry out the method of claim 1.

13. Data-processing apparatus, having a processor, for normalizing an individual mention of a subcellular entity within a biomedical text document, said data-processing apparatus comprising:

an input module for inputting said individual mention of a subcellular entity;

a first selection module for selecting a group of identifiers of subcellular entities, said subcellular entities being referred to in biomedical text with the same character string and being from different species, each of said species being a taxonomic group of organisms which can interbreed;

an identification module for generating, using said processor, a species identifier that identifies the species of said individual mention of a subcellular entity from the context of said mention of a subcellular entity;

a second selection module for selecting an identifier from said group of identifiers, taking into account the species identifier that identifies the species of said individual mention of a subcellular entity; and an output module for outputting said identifier to provide a normalized reference to said subcellular entity.

14. Data-processing apparatus according to claim 13, wherein the data-processing apparatus comprises a candidate identifier selection module which is operable to creating a group of one or more candidate identifiers by searching a lexicon comprising character strings which are used in biomedical text documents to refer to subcellular entities for character strings which match the individual mention of a subcellular entity, either as exact matches or using an approximate matching algorithm, and to include the identifiers of the matched subcellular entities in the group of one or more candidate identifiers.

15. Data-processing apparatus according to claim 14, wherein the lexicon comprises data concerning the species of subcellular entities having a particular identifier, wherein the data-processing apparatus is operable to determine whether the said group of one or more candidate identifiers comprises a plurality of candidate identifiers, and if so, to revise the group to produce a group comprising only identifiers, selected from the said group of one or more candidate identifiers, for which the species of the subcellular entity referred to by the identifiers is the identified species of the mention of the subcellular entity, thereby taking into account the identified species of the said individual mention of a subcellular entity.

16. Data-processing apparatus according to claim 15, wherein the second selection module is operable to select an identifier from the group of one or more candidate identifiers, or a revised group of candidate identifiers selected from the said group of one or more candidate identifiers, and to assign the selected identifier to an individual mention of a subcellular entity on the basis of a predetermined algorithm or heuristic.

17. Data-processing apparatus according to claim 16, wherein the second selection module is adapted to select an identifier from the group of one or more candidate identifiers on the basis of data which is known to be correlated to the likelihood that the identifier is the correct identifier of a protein mention.

18. Data-processing apparatus according to claim 16, wherein the predetermined algorithm or heuristic which is used by the second selection module to select an identifier from the group of one or more candidate identifiers selects an identifier on the basis of the values of the identifiers.

19. Data-processing apparatus according to claim 13, wherein the identification module comprises a machine trained algorithm which takes into account the text in a window around an individual mention of a subcellular entity in the biomedical text document.

20. Data-processing apparatus according to claim 13, wherein the identification module determines the species of the said individual mention of the subcellular entity by looking for species words which are close to the individual mention of a subcellular entity in the biomedical text document.

21. Data-processing apparatus according to claim 13, wherein the biomedical text document includes mentions of subcellular entities relating to more than one species of organism.

22. Data-processing apparatus according to claim 21, wherein at least one pair of the said mentions of subcellular entities is denoted by an identical characters string but relate to different species and the data-processing apparatus is operable, in at least some cases, to assign different identifiers to the said mentions of subcellular entities dependent on the species of the individual mentions of subcellular entities responsive to species determining contextual information around the said individual mentions of the species in the biomedical text document.

23. Data-processing apparatus according to claim 13, wherein the subcellular biological entity is a protein.

24. A non-transitory storage medium having program code instructions which, when executed on a computer having a processor, cause the computer to perform a method of normalizing an individual mention of a subcellular entity within a biomedical text document, the method comprising:

inputting said individual mention of a subcellular entity;

selecting a group of identifiers of subcellular entities, said subcellular entities being referred to in biomedical text with the same character string and being from different species, each of said species being a taxonomic group of organisms which can interbreed;

generating, using said processor, a species identifier that identifies the species of said individual mention of a subcellular entity from the context of said mention of a subcellular entity;

selecting an identifier from said group of identifiers, taking into account the species identifier that identifies the species of said individual mention of a subcellular entity; and outputting said identifier to provide a normalized reference to said subcellular entity.

* * * * *